United States Patent
Sopchik et al.

(10) Patent No.: US 11,098,000 B2
(45) Date of Patent: Aug. 24, 2021

(54) METHOD FOR RECOVERY OF METHACROLEIN AND METHANOL FROM METHACROLEIN DIMETHYLACETAL

(71) Applicants: Dow Global Technologies LLC, Midland, MI (US); Rohm and Haas Company, Collegeville, PA (US)

(72) Inventors: Alan E. Sopchik, Seabrook, TX (US); William G. Worley, Missouri City, TX (US); Rajesh Shah, League City, TX (US)

(73) Assignees: Dow Global Technologies LLC, Midland, MI (US); Rohm andHaas Company, Collegeville, PA (US)

( * ) Notice: Subject to any disclaimer, the term of this patent is extended or adjusted under 35 U.S.C. 154(b) by 0 days.

(21) Appl. No.: 16/644,571

(22) PCT Filed: Sep. 4, 2018

(86) PCT No.: PCT/US2018/049336
§ 371 (c)(1),
(2) Date: Mar. 5, 2020

(87) PCT Pub. No.: WO2019/050830
PCT Pub. Date: Mar. 14, 2019

(65) Prior Publication Data
US 2021/0061746 A1    Mar. 4, 2021

Related U.S. Application Data

(60) Provisional application No. 62/556,527, filed on Sep. 11, 2017.

(51) Int. Cl.
C07C 45/00  (2006.01)
C07C 29/00  (2006.01)
C07C 45/51  (2006.01)
C07C 29/09  (2006.01)

(52) U.S. Cl.
CPC .......... C07C 45/515 (2013.01); C07C 29/095 (2013.01)

(58) Field of Classification Search
CPC .......................... C07C 45/515; C07C 29/095
See application file for complete search history.

(56) References Cited

U.S. PATENT DOCUMENTS

| | | |
|---|---|---|
| 3,928,459 A | 12/1975 | Mercier |
| 4,579,979 A | 4/1986 | Degussa |
| 5,079,266 A | 1/1992 | Bockowski et al. |

FOREIGN PATENT DOCUMENTS

| | | |
|---|---|---|
| EP | 0150280 | 8/1985 |
| JP | 11302224 | 11/1999 |
| JP | 03532763 | 5/2004 |
| JP | 5818364 | 11/2015 |

OTHER PUBLICATIONS

Coppola, G.M., Synthesis, 1984, p. 1021.

*Primary Examiner* — Sikarl A Witherspoon
(74) *Attorney, Agent, or Firm* — Brian L. Mutschler

(57) ABSTRACT

A process for recovering methacrolein and methanol from methacrolein dimethyl acetal. The method comprises a step of contacting a mixture comprising methyl methacrylate and methacrolein dimethyl acetal with a strong acid ion exchange resin in the presence of water. The mixture comprises no more than 0.2 wt % sodium methacrylate.

6 Claims, 1 Drawing Sheet

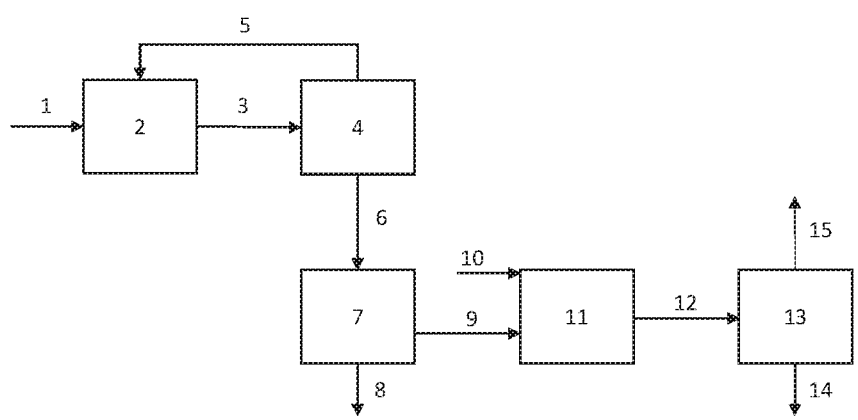

METHOD FOR RECOVERY OF METHACROLEIN AND METHANOL FROM METHACROLEIN DIMETHYLACETAL

BACKGROUND OF THE INVENTION

The invention relates to a process for recovery of methacrolein and methanol from methacrolein dimethylacetal, a reaction product from preparation of methyl methacrylate.

A significant process yield loss in preparation of methyl methacrylate (MMA) is formation of methacrolein dimethyl acetal (MDA) as a result of a side reaction of the key intermediate methacrolein (MA) with methanol. Conventionally, this is done by hydrolyzing MDA in the presence of a mineral acid, which is undesirable due to possible corrosion and the increased process complexity due to neutralization, catalyst disposal, and wastewater treatment requirements. Hydrolysis of acetals in the presence of ion exchange resins having sulfonic acid functionality is known, see, e.g., Coppola, G. M. *Synthesis* 1984, 1021. However, there has been no disclosure of MDA hydrolysis in the presence of acids other than mineral acids. There is a need for a more efficient process for recovering methacrolein and methanol from MDA resulting from preparation of methyl methacrylate.

SUMMARY OF THE INVENTION

The present invention is directed to a process for recovering methacrolein and methanol from methacrolein dimethyl acetal; said method comprising contacting a mixture comprising methyl methacrylate and methacrolein dimethyl acetal with a strong acid ion exchange resin in the presence of water; wherein said mixture comprises no more than 0.2 wt % sodium methacrylate.

BRIEF DESCRIPTION OF THE DRAWING

The FIGURE is a schematic of an integrated process for producing methyl methacrylate.

DETAILED DESCRIPTION OF THE INVENTION

All percentage compositions are weight percentages (wt %), and all temperatures are in ° C., unless otherwise indicated. A "strong acid ion exchange resin" is an ion exchange resin having sulfonic acid functionality. Preferably, the ion exchange resin is in the form of crosslinked polystyrene beads.

Preferably, the MDA is generated in a process which comprises treating methacrolein with methanol in an oxidative esterification reactor (OER). The reaction typically produces MMA and MDA, along with methacrylic acid and unreacted methanol. Preferably, the reaction products are fed to a methanol recovery distillation column which provides an overhead stream rich in methanol and methacrolein; preferably this stream is recycled back to the OER. The bottoms stream from the methanol recovery distillation column comprises MMA, MDA, methacrylic acid, salts and water. In one embodiment of the invention, MDA is hydrolyzed in a medium comprising MMA, MDA, methacrylic acid and water.

Preferably, the strong acid ion exchange resin is a macroreticular resin. Preferably, the resin is in the form of beads having a harmonic mean size from 100 to 1200 microns; preferably at least 300 microns, preferably at least 400 microns, preferably at least 500 microns; preferably no more than 1100 microns, preferably no more than 1000 microns, preferably no more than 900 microns, preferably no more than 800 microns. Preferably, the resin has an average pore diameter from 20 to 600 Å; preferably at least 50 Å, preferably at least 100 Å, preferably at least 200 Å; preferably no more than 500 Å. Preferably, the strong acid ion exchange resin is selected from the group consisting of AMBERLYST-15 resin, AMBERLYST 36, DOWEX DR-2030, DOWEX HCR-S, DOWEX HCR-W2, DOWEX HGR and DOWEX HGR-W2, DOWEX M-3, DOWEX G-26 and DOWEX 50WX series of resins. Preferably, the strong acid ion exchange resin is contained in a fluid or fixed bed in a continuous reactor.

Water is present when the strong acid ion exchange resin is contacted with MDA and MMA. The source of the water is the process stream comprising MMA and MDA, water which is added to the MDA and MMA, the strong acid ion exchange resin, or a combination thereof.

At least a portion of salts generated as byproducts (e.g., sodium methacrylate) is removed prior to contacting the OER reaction mixture with the strong acid ion exchange resin, preferably at least 50 wt % of the salts, preferably at least 75 wt %, preferably at least 90 wt %, preferably at least 95 wt %, preferably substantially all of the salts. Preferably, the concentration of sodium methacrylate in mixture comprising methyl methacrylate and methacrolein dimethyl acetal is no greater than 0.15 wt %, preferably no greater than 0.1 wt %, preferably no greater than 0.05 wt %, preferably no greater than 0.02 wt %.

The present invention is further directed to an integrated process for production of methyl methacrylate. MDA may be hydrolyzed by separating the bottoms stream from a methanol recovery distillation column; said stream comprising MMA, MDA, methacrylic acid, salts and water; and performing the hydrolysis in the organic phase. It may be necessary to add water to the organic phase to ensure that there is sufficient water for the MDA hydrolysis; these amounts may be determined easily from the composition of the organic phase. The product of the MDA hydrolysis reactor is phase separated and the organic phase passes through one or more distillation columns to produce MMA product and light and/or heavy byproducts.

The FIGURE depicts an integrated process in which MDA hydrolysis occurs after phase separation of the bottoms stream from a methanol recovery column. Feed stream 1 enters OER 2 which produces product stream 3 which then passes into distillation column 4. The overhead stream 5 from column 4, which comprises methanol and methacrolein, is recycled to the OER, while bottoms stream 6 is sent to phase separator 7. Organic phase 9 is sent to acetal hydrolysis reactor 11 along with stream 10 comprising water, while aqueous phase 8 comprising water and salts is removed. Product 12 from reactor 11 goes into phase separator 13, with crude MMA product stream 15 passing into further purification while aqueous layer 14 is removed. Further purification of stream 15 by conventional distillation techniques provides methacrolein for recycle along with purified MMA.

Examples

Comparative examples of various strong organic and inorganic acids and heterogeneous AMBERLYST-15 resin catalyzed MDA hydrolysis are given below, Table 1. Hydrolysis experiments using mineral and organic acids were performed by charging a reaction flask with MMA and MDA, heating to 60° C., then adding an aqueous acid charge. Reactions using AMBERLYST-15 resin catalysis first combined MMA, MDA, and Amberlyst-15 resin, heated to 60° C., then the water was added. The progress of the hydrolysis was monitored using gas chromatography (GC) of the upper organic layer.

TABLE 1

Acid catalyzed MDA Hydrolysis at 60° C.*

| | | MDA in organic phase (wt %) | | | | |
|---|---|---|---|---|---|---|
| Exp. | wt % acid | 0 min | 5 min | 30 min | 60 min | 120 min |
| 1 | 5% $H_3PO_4$ | 10.45 | 5.79 | — | 0.067 | 0.035 |
| 2 | 5% $H_2SO_4$ | 10.51 | 0.022 | — | 0.020 | 0.042 |
| 3 | 1% $H_2SO_4$ | 10.59 | 0.35 | 0.018 | — | — |
| 4 | 1% MSA | 10.40 | 0.019 | 0.017 | — | — |
| 5 | 2% pTSA | 10.46 | 0.020 | 0.018 | 0.037 | — |
| 6 | 4% MAA | 10.30 | 4.20 | 0.079 | 0.014 | 0.014 |
| 7 | AMBERLYST -15 | 10.43 | 0.40 | 0.022 | 0.017 | 0.019 |

*Amberlyst 15 dry (≥4.7 eq/kg) was used without pre-swelling prior to use.

Experimentally, the equilibrium limit appeared to be about 180-ppm acetal at 60° C. if methanol and methacrolein are not removed during the reaction. The MDA concentration used in this study is approximately 10-fold greater than that expected in the bottom of the MeOH Recovery Column.

Results

Phosphoric Acid

Phosphoric acid hydrolysis kinetics was much slower compared to all other acids even at high 5% phosphoric acid levels.

Sulfuric Acid and Methanesulfonic Acid (MSA)

MSA and sulfuric acid kinetics were both faster than phosphoric acid. At 5 wt % sulfuric acid, the reaction reached near equilibrium within 5 minutes. At 1 wt %, hydrolysis using both sulfuric and methanesulfonic acids reached equilibrium in about 30 minutes.

p-Toluenesulfonic Acid (pTSA)

pTSA was used as the monohydrate. To compare the hydrolysis rates of pTSA with MSA on a similar molar basis, a 2 wt % pTSA solution was used. The reaction rates for MSA and pTSA were similar, each reaching equilibrium within ~30 minutes.

Methacrylic Acid (MAA)

MMA process impurity methacrylic acid, was screened for hydrolysis catalyst activity. MAA is present in the Methanol Recovery Column, but typically only at very low levels. For demonstration purposes, an MDA hydrolysis reaction was carried out using 4% MAA. MAA catalyzed MDA hydrolysis albeit at an almost two-fold slower rate compared to the other acids studied here.

Amberlyst-15

AMBERLYST-15 (dry) IER resin was used for this example. Based on Amberlyst-15≥4.7 eq/kg, the IER sulfonic acid content used here was about four times that in 2% pTSA experiments. The rate of Amberlyst-15 catalyzed acetal hydrolysis at both the 5 and 30-minute intervals were similar to those using 1% sulfuric acid. Equilibrium was reached within 30 min.

Effect of Salts

Additional hydrolysis experiments were conducted as described above, but with 0.48% sodium methacrylate (NaMAA) in the mixture. With 0.2% MSA there was no detectable conversion in two hours. With AMBERLYST-15 (dry) IER resin (0.41 g in 20.07 g total mixture) the conversion was only 13% in two hours. A control experiment with 0.2% MSA without salt led to 99% conversion in five minutes.

The invention claimed is:

1. A process for recovering methacrolein and methanol from methacrolein dimethyl acetal; said method comprising contacting a mixture comprising methyl methacrylate, sodium methacrylate, and methacrolein dimethyl acetal with a strong acid ion exchange resin in the presence of water; wherein said mixture comprises no more than 0.2 wt % sodium methacrylate.

2. The process of claim 1 wherein the strong acid ion exchange resin is a macroreticular resin.

3. The process of claim 2 wherein the strong acid ion exchange resin is in the form of beads having a harmonic mean size from 100 to 1200 microns.

4. The process of claim 2 wherein the strong acid ion exchange resin is contained in a fluid or fixed bed in a continuous reactor.

5. The process of claim 2 wherein the strong acid ion exchange resin has an average pore diameter from 20 to 600 Å.

6. The process of claim 1 wherein said mixture comprises no more than 0.1 wt % sodium methacrylate.

* * * * *